United States Patent
MacLaughlin et al.

(10) Patent No.: US 11,215,546 B2
(45) Date of Patent: Jan. 4, 2022

(54) ANTIMICROBIAL PARTICLE DETECTORS

(71) Applicant: Particle Measuring Systems, Inc., Boulder, CO (US)

(72) Inventors: Scott MacLaughlin, Boulder, CO (US); Jon Skuba, Boulder, CO (US)

(73) Assignee: PARTICLE MEASURING SYSTEMS, INC., Boulder, CO (US)

( * ) Notice: Subject to any disclaimer, the term of this patent is extended or adjusted under 35 U.S.C. 154(b) by 0 days.

(21) Appl. No.: 17/063,797

(22) Filed: Oct. 6, 2020

(65) Prior Publication Data

US 2021/0102884 A1    Apr. 8, 2021

Related U.S. Application Data

(60) Provisional application No. 63/065,916, filed on Aug. 14, 2020, provisional application No. 63/023,535, (Continued)

(51) Int. Cl.
*G01N 15/06* (2006.01)
*G01N 15/00* (2006.01)

(52) U.S. Cl.
CPC . *G01N 15/0631* (2013.01); *G01N 2015/0023* (2013.01); *G01N 2015/035* (2013.01)

(58) Field of Classification Search
CPC ... A61B 6/4423; A61B 6/4283; A61B 6/4405; A61L 2/088; A61L 2/238; B82Y 30/00;
(Continued)

(56) References Cited

U.S. PATENT DOCUMENTS 4,594,715 A    6/1986   Knollenberg
4,798,465 A    1/1989   Knollenberg
(Continued)

FOREIGN PATENT DOCUMENTS

EP    1996744    2/2011

OTHER PUBLICATIONS

Biswas et al. (1984) "High-velocity inertial impactors," Environ. Sci. Technol. 18(8): 611-616.
(Continued)

*Primary Examiner* — Hoa Q Pham
(74) *Attorney, Agent, or Firm* — Leydig, Voit & Mayer, Ltd.

(57) ABSTRACT

The invention generally provides systems and methods for particle detection for minimizing microbial growth and cross-contamination in manufacturing environments requiring low levels of microbes, such as cleanroom environments for electronics manufacturing and aseptic environments for manufacturing pharmaceutical and biological products, such as sterile medicinal products. In some embodiments, systems of the invention incorporate a housing having an outer surface being a first antimicrobial surface and a touchscreen being a second antimicrobial surface. In some embodiments, substantially all of the outer surfaces of the system are antimicrobial surfaces. In some embodiments, the first antimicrobial surface may comprise an Active Screen Plasma alloyed layer. In some embodiments, the housing may comprise a molded polymer substrate and a metal coating layer bonded to the molded polymer substrate such that at least some exterior surfaces of the housing are metal coated surfaces.

21 Claims, 3 Drawing Sheets

Related U.S. Application Data filed on May 12, 2020, provisional application No. 62/911,801, filed on Oct. 7, 2019.

(58) Field of Classification Search
CPC .......... A01N 59/16; G01N 2015/1486; G01N 2015/1037; G01N 2015/1493; G01N 2015/1087; G01N 15/12; G01N 15/47; G01N 15/02; G01N 15/10; G01N 21/49
USPC ................ 356/335–343, 73, 237.1–237.5
See application file for complete search history.

(56) References Cited

U.S. PATENT DOCUMENTS

| | | | |
|---|---|---|---|
| 4,893,928 A | 1/1990 | Knollenberg | |
| 5,037,522 A | 8/1991 | Vergason | |
| 5,157,678 A * | 10/1992 | Borden | G01N 21/53 |
| | | | 372/103 |
| 5,282,151 A | 1/1994 | Knollenberg | |
| 5,283,199 A | 2/1994 | Bacon, Jr. et al. | |
| 5,671,046 A | 9/1997 | Knowlton | |
| 5,726,753 A | 3/1998 | Sandberg | |
| 5,751,422 A | 5/1998 | Mitchell | |
| 5,805,281 A | 9/1998 | Knowlton et al. | |
| 5,861,950 A | 1/1999 | Knowlton | |
| 5,889,589 A | 3/1999 | Sandberg | |
| 5,903,338 A | 5/1999 | Mavliev et al. | |
| 6,167,107 A | 12/2000 | Bates | |
| 6,246,474 B1 | 6/2001 | Cerni et al. | |
| 6,275,290 B1 | 8/2001 | Cerni et al. | |
| 6,615,679 B1 | 9/2003 | Knollenberg et al. | |
| 6,709,311 B2 | 3/2004 | Cerni | |
| 6,859,277 B2 | 2/2005 | Wagner et al. | |
| 6,903,818 B2 | 6/2005 | Cerni et al. | |
| 6,929,705 B2 * | 8/2005 | Myers | A01N 25/34 |
| | | | 106/813 |
| 6,945,090 B2 | 9/2005 | Rodier | |
| 7,030,980 B1 | 4/2006 | Sehler et al. | |
| 7,088,446 B2 | 8/2006 | Cerni | |
| 7,088,447 B1 | 8/2006 | Bates et al. | |
| 7,208,123 B2 | 4/2007 | Knollenberg et al. | |
| 7,235,214 B2 | 6/2007 | Rodier et al. | |
| RE39,783 E | 8/2007 | Cerni et al. | |
| 7,456,960 B2 | 11/2008 | Cerni et al. | |
| 7,576,857 B2 | 8/2009 | Wagner | |
| 7,667,839 B2 | 2/2010 | Bates | |
| 7,746,469 B2 | 6/2010 | Shamir et al. | |
| 7,796,255 B2 | 9/2010 | Miller | |
| 7,916,293 B2 | 3/2011 | Mitchell et al. | |
| 7,973,929 B2 | 7/2011 | Bates | |
| 7,985,949 B2 | 7/2011 | Rodier | |
| 8,027,035 B2 | 9/2011 | Mitchell et al. | |
| 8,109,129 B2 | 2/2012 | Gorbunov | |
| 8,154,724 B2 | 4/2012 | Mitchell et al. | |
| 8,174,697 B2 | 5/2012 | Mitchell et al. | |
| 8,414,577 B2 | 4/2013 | Boudreaux et al. | |
| 8,427,642 B2 | 4/2013 | Mitchell et al. | |
| 8,800,383 B2 | 8/2014 | Bates | |
| 8,869,593 B2 | 10/2014 | Gorbunov et al. | |
| 9,500,591 B1 | 11/2016 | Goad et al. | |
| 9,580,817 B2 | 2/2017 | Smith et al. | |
| 9,631,222 B2 | 4/2017 | Ketcham et al. | |
| 9,638,665 B2 | 5/2017 | Gorbunov | |
| 9,682,345 B2 | 6/2017 | Gromala et al. | |
| 9,808,760 B2 | 11/2017 | Gromala et al. | |
| 9,810,558 B2 | 11/2017 | Bates et al. | |
| 9,885,640 B2 | 2/2018 | Ketcham et al. | |
| 9,989,462 B2 | 6/2018 | Lumpkin et al. | |
| 10,197,487 B2 | 2/2019 | Knollenberg et al. | |
| 10,278,390 B2 * | 5/2019 | Rolfe | A01N 25/28 |
| 10,345,200 B2 | 7/2019 | Scialo et al. | |
| 10,371,620 B2 | 8/2019 | Knollenberg et al. | |
| 10,405,818 B2 * | 9/2019 | Langley | A61L 2/088 |
| 10,792,694 B2 | 10/2020 | Gorbunov et al. | |
| 10,859,487 B2 | 12/2020 | Knollenberg et al. | |
| 10,908,059 B2 | 2/2021 | Knollenberg et al. | |
| 10,921,229 B2 | 2/2021 | Shamir | |
| 10,928,293 B2 | 2/2021 | Knollenberg et al. | |
| 2005/0028593 A1 | 2/2005 | Rodier | |
| 2006/0134313 A1 | 6/2006 | Guggenbichler et al. | |
| 2006/0259020 A1 | 11/2006 | Sharratt | |
| 2008/0174570 A1 | 7/2008 | Jobs et al. | |
| 2009/0078862 A1 | 3/2009 | Rodier et al. | |
| 2009/0130157 A1 * | 5/2009 | Ylitalo | B32B 7/06 |
| | | | 424/405 |
| 2009/0190128 A1 | 7/2009 | Cerni et al. | |
| 2009/0268202 A1 | 10/2009 | Wagner | |
| 2013/0209718 A1 | 8/2013 | Wen | |
| 2015/0000595 A1 | 1/2015 | Gorbunov et al. | |
| 2015/0202842 A1 | 7/2015 | Dong et al. | |
| 2015/0259723 A1 | 9/2015 | Hartigan et al. | |
| 2015/0316463 A1 | 11/2015 | Pariseau et al. | |
| 2015/0320035 A1 | 11/2015 | Trinder, II et al. | |
| 2016/0126081 A1 | 5/2016 | Gorbunov | |
| 2016/0139013 A1 | 5/2016 | Gorbunov | |
| 2017/0011575 A1 * | 1/2017 | Sotereanos | G07C 13/00 |
| 2017/0248509 A1 | 8/2017 | Godoy et al. | |
| 2018/0185097 A1 | 7/2018 | Langhorn et al. | |
| 2018/0236118 A1 * | 8/2018 | Arora | A61L 2/238 |
| 2019/0250785 A1 * | 8/2019 | Pandolfi | G01C 21/206 |
| 2019/0338410 A1 | 11/2019 | Ruben et al. | |
| 2019/0339186 A1 | 11/2019 | Remiarz et al. | |
| 2019/0346345 A1 | 11/2019 | Scialo et al. | |
| 2020/0072729 A1 | 3/2020 | Lumpkin et al. | |
| 2020/0150017 A1 | 5/2020 | Bates et al. | |
| 2020/0150018 A1 | 5/2020 | Shamir | |
| 2020/0158603 A1 | 5/2020 | Scialo et al. | |
| 2020/0240896 A1 | 7/2020 | Karasikov et al. | |
| 2020/0355599 A1 | 11/2020 | Rodier et al. | |
| 2021/0044978 A1 | 2/2021 | Michaelis et al. | |
| 2021/0063349 A1 | 3/2021 | Rodier et al. | |
| 2021/0102884 A1 | 4/2021 | MacLaughlin et al. | |
| 2021/0104146 A1 | 4/2021 | MacLaughlin et al. | |
| 2021/0136722 A1 | 5/2021 | Scialo et al. | |
| 2021/0140867 A1 | 5/2021 | Knollenberg et al. | |
| 2021/0190659 A1 | 6/2021 | Knollenberg et al. | |

OTHER PUBLICATIONS

Comark Instruments, "BioCote Antimicrobial Protection," accessed on Jun. 5, 2019 at https://www.comarkinstruments.net/biocote-antimicrobial-protection/, 5 pp.

International Search Report and Written Opinion, dated Feb. 17, 2021, corresponding to International Patent Application No. PCT/US2020/054331, 14 pages.

Mono TRIO.BAS, Hardy Diagnostics, TRIO.BAS microbial air samplers, http://hardydiagnostics.com/triobas/, webpage publicly available at least as early as Jun. 5, 2019, 2 pp.

* cited by examiner

ANTIMICROBIAL PARTICLE DETECTORS

CROSS-REFERENCE TO RELATED APPLICATIONS

This application claims the benefit of priority to U.S. Provisional Application Ser. No. 62/911,801, filed Oct. 7, 2019, U.S. Provisional Application Ser. No. 63/023,535, filed May 12, 2020, and U.S. Provisional Application Ser. No. 63/065,916, filed Aug. 14, 2020, each of which is incorporated by reference in its entirety.

BACKGROUND OF INVENTION

This invention is in the field of particle sampling, collection and analysis. This invention relates generally to particle detectors having antimicrobial surfaces for reducing contamination and controlling microbial growth in controlled environments.

Cleanrooms and clean zones are commonly used in semiconductor and pharmaceutical manufacturing facilities. For the semiconductor industry, an increase in airborne particulate concentration can result in a decrease in fabrication efficiency, as particles that settle on semiconductor wafers will impact or interfere with the small length scale manufacturing processes. For the pharmaceutical industry, where this type of real-time efficiency feedback is lacking, contamination by airborne particulates and biological contaminants puts pharmaceutical products at risk for failing to meet cleanliness level standards established by the US Food and Drug Administration (FDA) and other foreign and international health regulatory agencies.

Standards for the classification of cleanroom particle levels and standards for testing and monitoring to ensure compliance are provided by ISO 14664-1 and 14664-2. Aerosol optical particle counters are commonly used to determine the airborne particle contamination levels in cleanrooms and clean zones, and liquid particle counters are used to optically measure particle contamination levels in process fluids. Where microbiological particles are a particular concern, such as in the pharmaceutical industry, not only is quantification of the number of airborne particles important, but characterizing the viability and identity of microbiological particles is also at issue. ISO 14698-1 and 14698-2 provide standards for evaluation of cleanroom and clean zone environments for biocontaminants.

Currently, collection and analysis of airborne biological particles is commonly achieved using a variety of techniques including settling plates, contact plates, surface swabbing, fingertip sampling and impactor-based active air samplers. Cascade impactors have traditionally been used for collection and sizing of particles. In these devices, a series of accelerations and inertial impacts successively strip smaller and smaller particles from a fluid flow. Each stage of an inertial impactor operates on the principle that particles suspended in air can be collected by forcing a dramatic change in the direction of the particle-containing airflow, where the inertia of the particle will separate the particle from the airflow streamlines and allow it to impact on the surface. Biswas et al. describe the efficiency at which particles can be collected in a high velocity inertial impactor (*Environ. Sci. Technol.*, 1984, 18(8), 611-616)

As requirements for lower viable and non-viable particle concentrations increase because of increased quality standards and governmental regulatory requirements, there is a need for advancement in sampling technology in order to reduce the risk of outside contamination from human interactions within the controlled environment. Humans are the largest source for clean room contaminants, accounting for up to 80% of particles and microbes generated in a room. Because the exterior surfaces of particle sampling instruments are in common and constant contact with humans due to transport (i.e. handle) and operation (i.e. touchscreen), halting microbial growth on the instrument itself would reduce overall room contaminants and cross-contamination when an instrument is transported to another clean room.

Maintaining sterile processing operations in aseptic manufacturing and cleanroom environments is required in a number of industries such as pharmaceuticals, biopharmaceuticals, parenteral drugs and medical devices, and microfabrication among others. Maintaining operations under stringent specifications for particulate matter and biological load can be critical to successful manufacturing in each of these industries.

In these highly regulated environments, it is critical that unwanted bacteria and/or other microorganisms do not contaminate the product. Therefore, contamination monitoring instruments that can detect viable and non-viable particles may often be housed in 316L Stainless Steel enclosures. 316L Stainless Steel (316L SST) is the "industry standard" for pharmaceutical manufacturers due to its ability to withstand repeated disinfections and wash-downs with harsh bacteria-killing chemicals and detergents, ease of cleaning, corrosion resistance, inert to alkalis and acids, chemical bacteriological neutrality, etc. 316L SST is also relatively easy to fabricate into enclosures, as its general forming and welding characteristics are good.

However, although stainless steel may visibly look like it is clean, it can still harbor bacterial pathogens invisible to the naked eye. Likewise, it cannot be determined how long a "cleaned" surface will remain free from bacteria. Furthermore, 316L stainless steel may be expensive and/or hard to fabricate and form into complex shapes. Additionally, it may be heavy and thus not optimal for handheld or mobile devices.

It can be seen from the foregoing that there remains a need in the art for particle collection, analysis, and characterization systems for sampling and collecting particles and/or organisms from controlled environments with reduced risk of microbial contamination and cross-contamination from one location to another by means of the particle collection instrument.

SUMMARY OF THE INVENTION

Provided herein are systems and methods for particle detection for minimizing microbial growth and cross-contamination. In one embodiment, a particle detection device comprises an inlet for receiving a particle-containing fluid, a sampling region for detecting particles, an outlet for discharging the fluid, a housing at least partially enclosing the sampling region, and a touchscreen disposed in the housing. The sampling region may be in fluid communication with the inlet. The outlet may be in fluid communication with the sampling region. The housing may have an exterior. The outer exterior of the housing may comprise a first antimicrobial surface. The touchscreen may provide a user interface with the device. The touchscreen may comprise a second antimicrobial surface.

In one embodiment, the exterior comprises a base layer. The base layer may include stainless steel. A first antimicrobial surface may comprises an outer layer deposited on the base layer. The outer layer may include an antimicrobial component. In one embodiment, the outer layer is a layer that has been deposited via an active screen plasma process. In one embodiment, the housing comprises a molded polymer substrate and a metal coating layer bonded to the molded polymer substrate such that at least some exterior surfaces of the housing are metal coated surfaces.

In some embodiments, the particle detection device may comprise a portable particle detection device. In some embodiments, the particle detection device may comprise a particle sampler or a particle counter. In some embodiments, the particle detection device may comprise a microbial impactor or an optical particle counter.

In some embodiments, the first antimicrobial surface may comprise the same material as the second antimicrobial surface. In some embodiments, the first antimicrobial surface comprises a different material as the second antimicrobial surface. In some embodiments, the first antimicrobial surface, second antimicrobial surface or both are antibacterial surfaces.

In some embodiments, at least a portion of the first antimicrobial surface, second antimicrobial surface or both are provided as integral components of the device. In some embodiments, at least a portion of the first antimicrobial surface, second antimicrobial surface or both are provided as one or more film or coating. In some embodiments, the first antimicrobial surface, second antimicrobial surface or both are a nano-patterned or micro-patterned bacterial growth inhibitor surface.

In some embodiments, the antimicrobial surface may be a photoactive antimicrobial surface. For example, the antimicrobial surface may comprise titanium dioxide configured to produce reactive oxygen species at the surface. In some embodiments, the antimicrobial surface may comprise a continuous antimicrobial coating. In some embodiments, the antimicrobial surface may comprise dispersed nanoparticles of an antimicrobial component.

In some embodiments, the antimicrobial surface may comprise an anti-adhesive component. The anti-adhesive component may prevent or deter bacteria and other microbes from adhering to the surface. In one embodiment, the anti-adhesive component comprises brush polymers. In one embodiment, the anti-adhesive component comprises nano-patterned or micro-patterned surface configured to deter or prevent microbes from adhering to the surface.

In some embodiments, the first antimicrobial surface, second antimicrobial surface or both comprise an antimicrobial polymer. In some embodiments, the antimicrobial polymer comprises silver ions. In some embodiments, the antimicrobial polymer comprises zinc.

In some embodiments, substantially all of the outer surfaces of the device are antimicrobial surfaces. In some embodiments, substantially all of the outer surfaces of the touchscreen are antimicrobial surfaces. In some embodiments, the housing comprises a handle, wherein substantially all of the outer surfaces of the handle are antimicrobial surfaces.

In one embodiment, a method of reducing microbial contamination in a clean room comprises the steps of operating a particle detection device, introducing a first microbe onto an antimicrobial surface of a housing of the device, inhibiting growth of the first microbe or killing the first microbe via the antimicrobial surface of the housing, introducing a second microbe onto an antimicrobial surface of a touchscreen of the device, inhibiting growth of the second microbe or killing the second microbe via the antimicrobial surface of the touchscreen. The housing may at least partially enclose the sampling region. The operating step may comprise introducing a particle-containing fluid to an inlet of the device; sampling particles in the fluid in a sampling region of the device; and discharging the fluid via an outlet of the device.

In some embodiments, the device is an optical particle detector and the sampling step comprises detecting particles via scattered light in the sampling region of the device.

In some embodiments, the device is a microbial impactor, the particle-containing fluid contains biological particles, and the sampling step comprises receiving at least a portion of the biological particles on an impact surface of the device; and growing at least some of the biological particles received by the impact surface.

In some embodiments, the first microbe is a bacteria, a virus, a mold, or a fungus.

In one aspect, the housing of particle detection system may comprise stainless steel. Antimicrobial components may be applied to the stainless steel of the housing via Active Screen Plasma (ASP), thereby alloying the exterior surfaces of the stainless steel housing. This Active Screen Plasma alloying may impart long-lasting antimicrobial properties to prevent the growth of bacteria and/or other microorganisms.

In one embodiment, a particle detection system comprises an inlet for receiving a particle-containing fluid, a sampling region for detecting particles, an outlet for discharging the fluid, and a housing at least partially enclosing the sampling region. The sampling region is in fluid communication with the inlet. The outlet is in fluid communication with the sampling region. The housing includes an exterior comprising a base layer comprising stainless steel and an outer layer deposited on the base layer.

The outer layer may comprise an antimicrobial component. In one embodiment, the outer layer comprises and an active screen plasma deposited outer layer comprising the antimicrobial component.

In one embodiment, the outer layer forms a first antimicrobial surface and the system may further include a touchscreen disposed in the housing, the touchscreen providing a user interface with the device, wherein the touchscreen comprises a second antimicrobial surface. In one embodiment, the housing comprises a molded polymer substrate supporting the base layer and the outer layer, and wherein the base layer is bonded to the molded polymer substrate.

In one embodiment, the antimicrobial component comprises copper. In one embodiment, the antimicrobial component comprises silver. In one embodiment, the antimicrobial component comprises at least one of, cobalt, nickel, zinc or zirconium.

In one embodiment, the outer layer has thickness of 1 um to 30 um. In one embodiment, the outer layer has thickness of 3 um to 24 um. In one embodiment, the outer layer has thickness of 5 um to 20 um.

In one embodiment, the outer layer has an HV 0.05 hardness of at least 1300. In one embodiment, the outer layer has an HV 0.05 hardness of at least 1350. In one embodiment, the outer layer has an HV 0.05 hardness of at least 1400.

In one embodiment, the system comprises a portable particle detection device. In another embodiment, the system comprises a stationary particle detection device. In one embodiment, the system comprises a particle sampler or a particle counter. In one embodiment, the system comprises a microbial impactor or an optical particle counter.

In one embodiment, the system comprises a particle counter configured to detect viable biological particles.

In one embodiment, the particle-containing fluid is a gas. In one embodiment, the particle-containing fluid is a liquid.

In one embodiment, the base layer comprises 316 stainless steel. In one embodiment, the base layer comprises 316L stainless steel.

In one embodiment, the outer layer comprises a nano-patterned or micro-patterned bacterial growth inhibitor surface.

In one embodiment, a method of reducing microbial contamination in a clean room comprises operating a particle detection system, introducing a first microbe onto a surface of a housing of the system, and inhibiting growth of the first microbe or killing the first microbe via an antimicrobial component. The operating may comprise introducing a particle-containing fluid to an inlet of the system, sampling particles in the fluid in a sampling region of the system, and discharging the fluid via an outlet of the system. The housing may at least partially enclose the sampling region. The housing includes an exterior. The exterior comprises a base layer of stainless steel having an outer surface; and an active screen plasma deposited outer layer comprising the antimicrobial component.

In one embodiment, the system for reducing microbial contamination in a clean room comprises an optical particle detector, and the sampling step comprises detecting particles via scattered light in the sampling region of the system.

In one embodiment, the system comprises a microbial impactor and the particle-containing fluid contains biological particles. In this embodiment, the sampling step may comprise receiving at least a portion of the biological particles on an impact surface of the system, and growing at least some of the biological particles received by the impact surface.

In one embodiment, the system comprises a portable particle detection system, and the step of introducing a first microbe is performed in a first location. In this embodiment, the method of reducing microbial contamination in a clean room comprises transporting the device to a second location, remote of the first location. This transporting step may take place after the step of inhibiting growth.

In one embodiment, a particle detection system comprises an inlet for receiving a particle-containing fluid; a sampling region for detecting particles, the sampling region in fluid communication with the inlet; an outlet for discharging the fluid, the outlet in fluid communication with the sampling region; and a housing at least partially enclosing the sampling region. The housing may comprise a molded polymer substrate; and a metal coating layer bonded to the molded polymer substrate such that at least some exterior surfaces of the housing are metal coated surfaces. The system may comprise a touchscreen disposed in the housing, the touchscreen providing a user interface with the device, wherein the touchscreen comprises an antimicrobial surface.

In one embodiment, the metal coating layer comprises a base layer comprising stainless steel, and an outer layer deposited on the base layer, where the outer layer comprises an antimicrobial component. In one embodiment, the outer layer is an active screen plasma deposited outer layer.

In one embodiment, the metal coating layer comprises stainless steel. In one embodiment, the metal coating layer comprises 316L stainless steel. In one embodiment, the metal coating layer comprises copper. In one embodiment, the metal coating layer comprises titanium. In one embodiment, the metal coating layer comprises silver. In one embodiment, the metal coating layer comprises at least one of: cobalt, nickel, zinc or zirconium.

In one embodiment, the metal coating layer has thickness of 0.01 mm to 1 mm. In one embodiment, the metal coating layer has thickness of 0.3 mm to 0.1 mm. In one embodiment, both the molded polymer substrate and the metal coating layer have a brushed texture. In one embodiment, both the molded polymer substrate and the metal coating layer have a nano-patterned or micro-patterned bacterial growth inhibitor texture.

In one embodiment, a method of reducing microbial contamination in a clean room comprises operating a particle detection system, the operating comprising: (a) introducing a particle-containing fluid to an inlet of the system; (b) sampling particles in the fluid in a sampling region of the system; (c) discharging the fluid via an outlet of the system; (d) introducing a first microbe onto a surface of a housing of the system, the housing at least partially enclosing the sampling region, wherein the housing comprises: a molded polymer substrate; and a metal coating layer bonded to the molded polymer substrate such that at least some exterior surfaces of the housing are metal coated surfaces; and (e) inhibiting growth of the first microbe or killing the first microbe via the metal coated surfaces.

In one embodiment, the system is an optical particle detector and the (b) sampling step comprises detecting particles via scattered light in the sampling region of the system. In one embodiment, the system is a microbial impactor, the particle-containing fluid contains biological particles, and the (b) sampling step comprises receiving at least a portion of the biological particles on an impact surface of the system; and growing at least some of the biological particles received by the impact surface.

In one embodiment, the system is a portable particle detection system, the (d) introducing a first microbe step is performed in a first location, and the method includes the step of: (f) after the (e) inhibiting growth step, transporting the device to a second location, remote of the first location.

In one embodiment, a particle detection system comprises an inlet for receiving a particle-containing fluid, a sampling region for detecting particles, an outlet for discharging the fluid, the outlet in fluid communication with the sampling region, a housing, and a touchscreen disposed in the housing. The housing may at least partially enclose the sampling region. The housing may include a molded polymer substrate and an exterior comprising a base layer, and an outer layer. The base layer may comprise stainless steel. The outer layer may be deposited on the base layer, for example via ASP. The outer layer may comprise an antimicrobial component. The molded polymer substrate may support the base layer and the outer layer. The base layer may be bonded to the molded polymer substrate. The touchscreen may provide a user interface with the device. The touchscreen may also comprises a second antimicrobial surface.

The devices and methods of the present invention are versatile and support a range of particle sampling, monitoring and analysis applications. For example, the present devices and methods are useful for applications involving preparation, handling, manufacture, storage, transfer, fill and/or finish of sterile pharmaceutical or biological agents, pharmaceutical or biological containers, pharmaceutical or biological delivery devices, medical devices including implantable devices, blood, cell and tissue materials. In addition, the present devices and methods are useful for monitoring and characterizing biological particles in healthcare environments, such as hospitals, operating rooms, surgical suites and compounding pharmacies. Other applications of the present devices and methods include the preparation, manufacture, storage, transfer or processing of cosmetics, personal care products, food and beverages.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1:
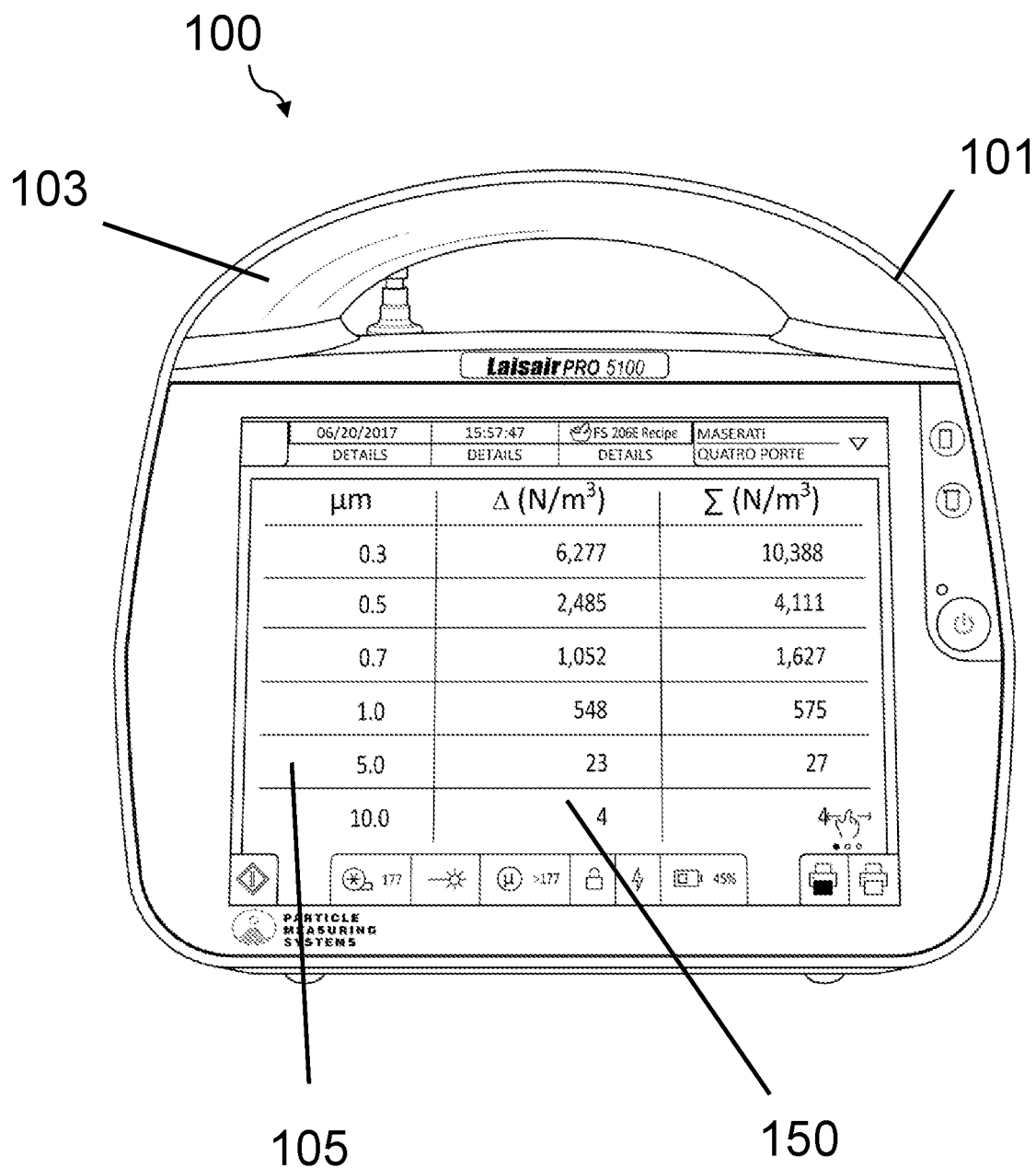
FIG. 1 is a front view of one embodiment of a particle detection device of the present invention, including a touch screen.

In general, the terms and phrases used herein have their art-recognized meaning, which can be found by reference to standard texts, journal references and contexts known to those skilled in the art. The following definitions are provided to clarify their specific use in the context of the invention.

"Particle" refers to a small object which is often regarded as a contaminant. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms. Biological particles include, but are not limited to, microorganisms having a size on the order of 0.1-20 μm. Biological particles include viable biological particles capable of reproduction, for example, upon incubation within a growth media. A particle may refer to any small object which absorbs or scatters light and is thus detectable by an optical particle counter. As used herein, "particle" is intended to be exclusive of the individual atoms or molecules of a carrier fluid, for example, such gases present in air (e.g., oxygen molecules, nitrogen molecules, argon molecule, etc.) or process gases. Some embodiments of the present invention are capable of sampling, collecting, detecting, sizing, and/or counting particles comprising aggregates of material having a size greater than 50 nm, 100 nm, 1 μm or greater, or 10 μm or greater. Specific particles include particles having a size selected from 50 nm to 50 μm, a size selected from 100 nm to 10 μm, or a size selected from 500 nm to 5 μm.

The expression "sampling a particle" broadly refers to collection of particles in a fluid flow, for example, from an environment undergoing monitoring. Sampling in this context includes transfer of particles in a fluid flow to an impact surface, for example, the receiving surface of a growth medium. Alternatively sampling may refer to passing particles in a fluid through a particle analysis region, for example, for optical detection and/or characterization. Sampling may refer to collection of particles having one or more preselected characteristics, such as size (e.g., cross sectional dimension such as diameter, effective diameter, etc.), particle type (biological or nonbiological, viable or nonviable, etc.) or particle composition. Sampling may optionally include analysis of collected particles, for example, via subsequent optical analysis, imaging analysis or visual analysis. Sampling may optionally include growth of viable biological particles, for sample, via an incubation process involving a growth medium. A sampler refers to a device for sampling particles.

"Impactor" refers to a device for sampling particles. In some embodiments, an impactor comprises a sample head including one or more intake apertures for sampling a fluid flow containing particles, whereby at least a portion of the particles are directed onto an impact surface for collection, such as the receiving surface of a growth medium (e.g., culture medium such as agar, broth, etc.) or a substrate such as a filter. Impactors of some embodiments, provide a change of direction of the flow after passage through the intake apertures, wherein particles having preselected characteristics (e.g., size greater than a threshold value) do not make the change in direction and, thus, are received by the impact surface.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these. A particle counter is a device for counting the number of particles in a fluid or volume of fluid, and optionally may also provide for characterization of the particles, for example, on the basis of size (e.g., cross sectional dimension such as diameter or effective diameter), particle type (e.g. biological or nonbiological), or particle composition. An optical particle counter is a device that detects particles by measuring scattering, emission or absorbance of light by particles.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Fluid communication" refers to the arrangement of two or more objects such that a fluid can be transported to, past, through or from one object to another. For example, in some embodiments two objects are in fluid communication with one another if a fluid flow path is provided directly between the two objects. In some embodiments, two objects are in fluid communication with one another if a fluid flow path is provided indirectly between the two objects, such as by including one or more other objects or flow paths between the two objects. For example, in one embodiment, the following components of a particle impactor are in fluid communication with one another: one or more intake apertures, an impact surface, a fluid outlet, a flow restriction, a pressure sensor, a flow generating device. In one embodiment, two objects present in a body of fluid are not necessarily in fluid communication with one another unless fluid from the first object is drawn to, past and/or through the second object, such as along a flow path.

"Flow rate" refers to an amount of fluid flowing past a specified point or through a specified area, such as through intake apertures or a fluid outlet of a particle impactor. In one embodiment a flow rate refers to a mass flow rate, i.e., a mass of the fluid flowing past a specified point or through a specified area. In one embodiment, a flow rate is a volumetric flow rate, i.e., a volume of the fluid flowing past a specified point or through a specified area.

"Pressure" refers to a measure of a force exhibited per unit area. In an embodiment, a pressure refers to a force exhibited by a gas or fluid per unit area. An "absolute pressure" refers to a measure of the pressure exerted by a gas or fluid per unit area as referenced against a perfect vacuum or volume exerting zero force per unit area. Absolute pressure is distinguished from a "differential pressure" or "gauge pressure", which refers to a relative change or difference in force exhibited per unit area in excess of or relative to a second pressure, such as an ambient pressure or atmospheric pressure.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyimide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

Figure 2:
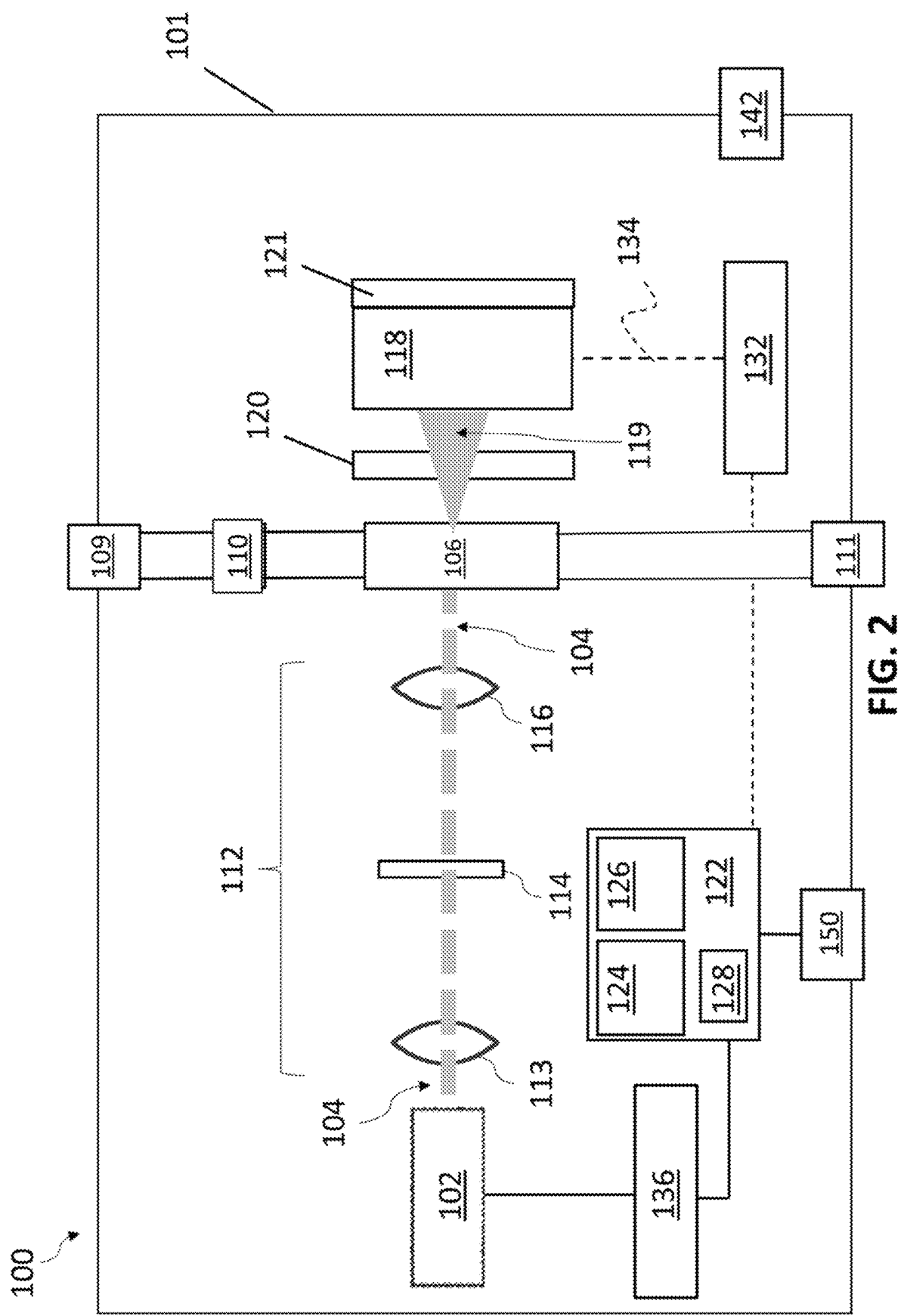
FIG. 2 is a schematic view of the particle detection device of FIG. 1.

FIGS. 1-2 show an embodiment of an example particle detection device, optical particle analyzer 100. The optical particle analyzer 100 includes an inlet 109 for receiving a particle-containing fluid, a sampling region 106 for detecting particles, and an outlet 111 for discharging the fluid. The sampling region 106 in fluid communication with the inlet 109. The outlet 111 is in fluid communication with the sampling region 106.

The optical particle analyzer 100 includes a housing 101 at least partially enclosing the sampling region 106, and a touchscreen 150 disposed in the housing 101. The housing 101 has an outer surface, the outer surface being a first antimicrobial surface to inhibit or prevent microbial growth. The touchscreen 150 provides a user interface with the device via an outer surface of the touchscreen, the touchscreen outer surface being a second antimicrobial surface to inhibit or prevent microbial growth.

In one embodiment, the first antimicrobial surface comprises the same material as the second antimicrobial surface. In another embodiment, the first antimicrobial surface comprises a different material as the second antimicrobial surface. In one embodiment, the first antimicrobial surface, second antimicrobial surface or both are antibacterial surfaces.

In some embodiments, the first antimicrobial surface, second antimicrobial surface or both are provided as integral components of the device. For example, in some embodiments, the first antimicrobial surface, second antimicrobial surface or both may be a nano-patterned or micro-patterned bacterial growth inhibitor surface. In one example, the first antimicrobial surface, second antimicrobial surface or both may be micropatterned surfaces such as those produced by SHARKET TECHNOLOGIES, Inc., of Aurora, Colo. Additionally or alternatively, the first antimicrobial surface, second antimicrobial surface or both comprise an antimicrobial polymer. In one example, the first antimicrobial surface, second antimicrobial surface or both may be an antimicrobial polymer such as those produced by STERITOUCH of Whales, UK. In one example, the antimicrobial polymer comprises silver ions. In one example, the antimicrobial polymer comprises zinc.

By fabricating at least a portion of the housing 101 from a polymer having antimicrobial properties, the difficulties of cost, formability and weight associated with 316L stainless steel may be overcome. Furthermore, prior art methods of instrument disinfection may comprise wiping the housing with disinfectant. The use of antimicrobial plastic provides an extra layer of protection in the event that such a manual operation misses areas, hard to reach places (corners, gaps, crevices, etc.). In this regard, the antimicrobial polymer housing may be a $2^{nd}$ line of defense.

In some embodiments, at least a portion of the first antimicrobial surface, second antimicrobial surface or both are provided as one or more film or coating. In some embodiments, at least a portion of the housing 101 and/or touchscreen 150 may be coated an antimicrobial epoxy, such as an epoxy containing an antibacterial and/or antifungal additive. In one example, a portion of the housing 101 and/or touchscreen 150 may be coated with AGION antimicrobial protected epoxy produced by BIO SHIELD TECH, LLC of Palm Coast, Fla.

In one embodiment, substantially all of the outer surfaces of the touchscreen are antimicrobial surfaces. In one embodiment, substantially all of the outer surfaces of the device are antimicrobial surfaces. In some embodiments, for example as shown in FIG. 1, the housing may comprise a handle. In some embodiments, substantially all of the outer surfaces of the handle are antimicrobial surfaces.

Devices of the present invention may be used to reduce microbial contamination in a clean room. For example, in one embodiment, a method of reducing microbial contamination in a clean room comprises the steps of operating an antimicrobial particle detection device, introducing a first microbe onto an antimicrobial surface of a housing of the device, introducing a second microbe onto an antimicrobial surface of a touchscreen of the device, and inhibiting growth or killing the first and second microbes.

The method of operating a particle detection device may comprise the steps of introducing a particle-containing fluid to an inlet of the device, sampling particles in the fluid in a sampling region of the device, and discharging the fluid via an outlet of the device. The housing may at least partially enclose the sampling region.

The particle detection device may comprise an optical particle detector, a particle sampler, a particle counter, or a microbial impactor.

In embodiments where the device is an optical particle detector, the sampling step may comprise detecting particles via scattered light in the sampling region of the device. In embodiments where the device is a microbial impactor and wherein the particle-containing fluid contains biological particles, the sampling step may comprise receiving at least a portion of the biological particles on an impact surface of the device, and growing at least some of the biological particles received by the impact surface.

In some embodiments, the first microbe is a bacteria, a virus, a mold, or a fungus. In some embodiments, the second microbe is a bacteria, a virus, a mold, or a fungus. In some embodiment, the first microbe is the same type of microbe as the second microbe. In some embodiments, the first microbe is a different type of microbe as the second microbe.

Turning to FIG. 2, the optical particle analyzer 100 includes a source of electromagnetic radiation ("EMR") 102 for generating a beam of EMR 104. In one embodiment, the source of EMR 102 includes at least one of a laser, a laser diode, a strip diode laser, a light emitting diode, and an incandescent lamp. In embodiments for which the source of EMR 102 includes the laser, the beam of EMR 104 includes a laser beam. In an embodiment, the laser includes at least one of a laser diode and a strip diode laser.

The optical particle analyzer 100 shown in FIGS. 1-2 includes a sampling region 106 for containing a sample medium and for receiving the beam of EMR 104. The sampling region is enclosed by the housing 101. In some embodiments the sampling region 106 receives the laser beam. The sample medium includes particles and a fluid (e.g., a liquid and/or gas). In an embodiment, the sampling region 106 includes a cuvette. In an embodiment, the sampling region 106 is a flow chamber for containing the sample medium and for receiving the beam of EMR 104. Optical particle analyzer 100 includes a flow inlet 109 and a flow outlet 111 for flowing the fluid through the flow chamber. In an embodiment, the optical particle analyzer 100 may include a filter 110 for filtering the fluid upstream (e.g., before the fluid enters an interior of the flow chamber through inlet 109) of the flow chamber. It is noted that in the case of airborne particles, the air stream of fluid making up the sample medium need not be confined within the sampling region 106.

The optical particle analyzer 100 shown in FIG. 2 includes an optical assembly 112 in optical communication with the source of EMR 102 for directing the beam of EMR 104 from the source of EMR 102 to the sampling region 106. In embodiments for which the source of EMR 102 comprises a laser, the optical assembly 112 may be in optical communication with the laser for directing the laser beam from the laser to the sampling region 106. In an embodiment, the optical assembly 112 may include one or more lenses, masks, and/or filters. In the illustrated embodiment, the optical assembly 112 includes a first lens 113, a mask 114, and a second lens 116 for focusing the beam of EMR 104 inside the sampling region 106. In embodiments for which the source of EMR 102 comprises a laser, the second lens 116 may focus the laser beam inside the sampling region 106.

The optical particle analyzer 100 shown in FIG. 2 includes a detector 118 for detecting scattered radiation 119 from the beam of EMR 104. In embodiments for which the source of EMR 102 includes the laser, the detector 118 detects scattered radiation 119 from the laser beam. The optical particle analyzer 100 includes an optical collection system 120 for directing the scattered radiation 119 from the beam of EMR 104 from the sampling region 106 and to the detector 118. In embodiments for which the source of EMR 102 includes the laser, the optical collection system 120 directs the scattered radiation 119 from the laser beam from the sampling region 106 and to the detector 118. In an embodiment, the optical particle analyzer 100 may include an additional detector for normalization (e.g., a normalization detector 121) for detecting light leaving the sampling region 106.

The optical particle analyzer 100 shown in FIG. 2 may include a computing system 122 having one or more processors 124 and one or more memory devices 126 operably connected to the one or more processors 124. The memory devices 126 include at least one non-transient processor-readable medium capable of storing program instructions encoded as software executable by processor(s) 124. The computing system 122 may include a user interface 128 for facilitating operational interactions and information visualizations and/or manipulations, e.g., via touchscreen display 150, a keyboard and/or other I/O devices by a user of the optical particle analyzer 100 with the computing device 122 and/or other components and subsystems of the optical particle analyzer 100.

The optical particle analyzer 100 shown in FIG. 2 may include amplification circuitry 132 operably coupled to the processor(s) 124 and operably coupled to the detector 118 for amplifying detector signals 134. The optical particle analyzer 100 may include drive circuitry 136 operably coupled to the processor(s) 124 and operably coupled to the source of EMR 102. In embodiments for which the source of EMR 102 includes the laser, the drive circuitry 136 is for the laser.

In an embodiment, processor(s) 124 may execute software stored in memory device(s) 126 for controlling various components of the optical particle analyzer 100 during operation. In an embodiment, the processor(s) 124 may control the source of EMR 102 via the drive circuitry 136 (e.g., by controlling user-specified frequencies, voltages, currents, waveforms, duty cycles, and other control parameters implemented by the drive circuitry 136). In an embodiment, the processor(s) 124 may provide instructions to control user-specified flow rates and other control parameters implemented by the flow system (not shown). In an embodiment, the processor(s) 124 may receive the detector signal 134 and, after decoding information encoded by the detector signals 134, store the decoded information in the memory device(s) 126. The optical particle analyzer 100 may include a power supply 142 for providing electric power to the various components and systems of the optical particle analyzer 100 requiring electric power to function.

Active Screen Plasma Alloying of Stainless Steel Surfaces of Particle Detectors

In one aspect, particle detection systems of the present invention may include one or more Stainless Steel surfaces. These stainless steel surfaces may be treated via active screen plasma (ASP) to add one more antimicrobial and/or antibacterial components to an outer layer of the stainless steel surface of a particle detection device. One example of a useful method of applying this outer layer is described in "Active screen plasma surface co-alloying of 316 austenitic stainless steel with both nitrogen and niobium for the application of bipolar plates in proton exchange membrane fuel cells" (International Journal of Hydrogen Energy, Volume 40, Issue 32, 24 Aug. 2015, Pages 10281-10292).

In one example, the particle detection system may comprise an inlet for receiving a particle-containing fluid, a sampling region for detecting particles, the sampling region in fluid communication with the inlet, an outlet for discharging the fluid, the outlet in fluid communication with the sampling region, and a housing at least partially enclosing the sampling region. The housing includes an exterior. The exterior of the housing includes a base layer of stainless steel having an outer surface. An outer layer, including one or more antimicrobial components, may be deposited onto the outer surface via an active screen plasma method. Such antimicrobial components can include copper, silver, cobalt, nickel, zinc and/or zirconium.

Figure 3:
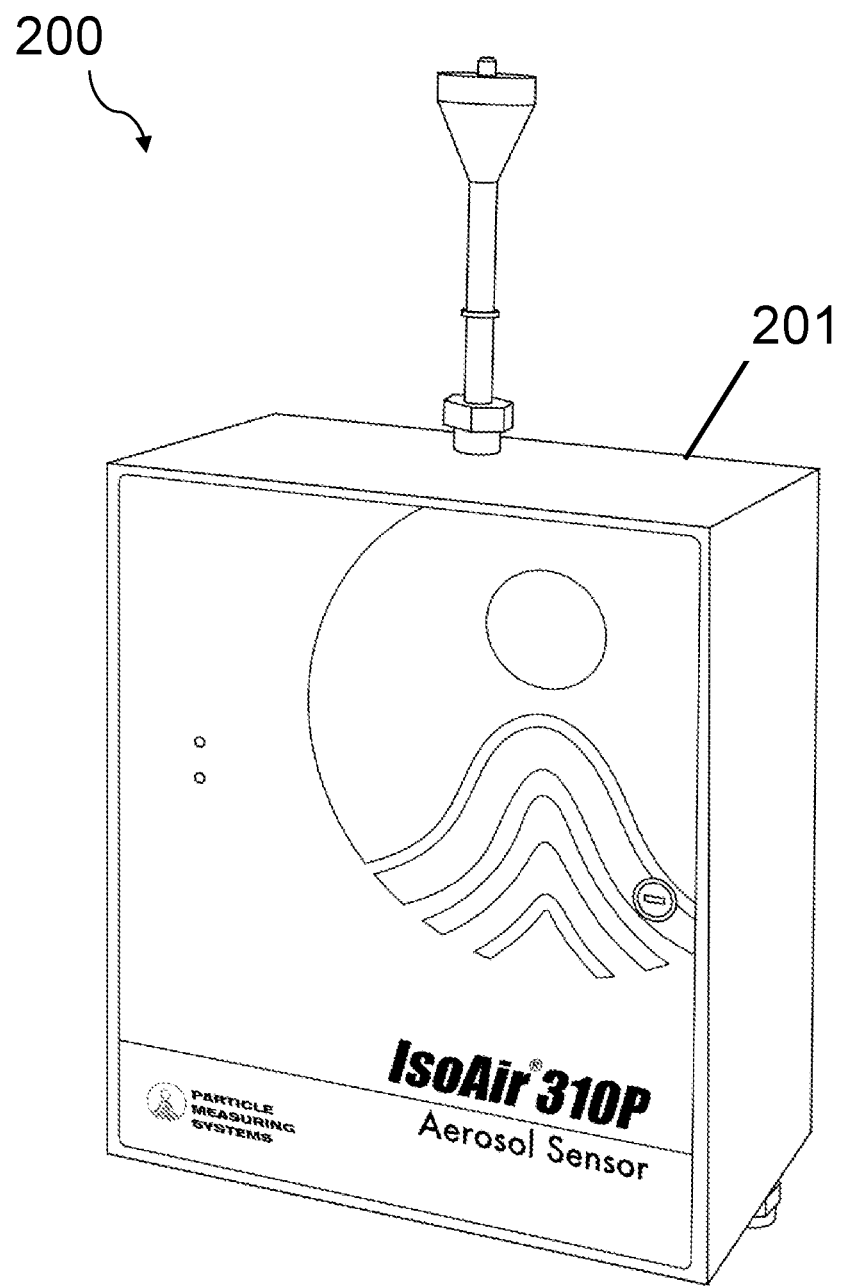
FIG. 3 is a front view of a second embodiment of a particle detection device of the present invention, including a stainless steel housing.

FIG. 3 shows one embodiment of a particle detection system 200 having a Stainless Steel housing 201.

In one embodiment, the outer layer has thickness of 1 um to 30 um. In one embodiment, the outer layer has thickness of 3 um to 24 um. In one embodiment, the outer layer has thickness of 5 um to 20 um.

In one embodiment, the outer layer has an HV 0.05 hardness of at least 1300. In one embodiment, the outer layer has an HV 0.05 hardness of at least 1350. In one embodiment, the outer layer has an HV 0.05 hardness of at least 1400.

The active screen plasma alloying may be useful across a variety of particle detection systems including portable particle detection devices, particle samplers, particle counters, microbial impactors, and optical particle counters. Such particle detection systems may be designed to detect particles on surfaces, in gases (including but not limited to air), and liquids.

In one embodiment, the outer layer comprises a nano-patterned or micro-patterned bacterial growth inhibitor surface. Thus, nano patterning may be employed synergistically with Active Screen Plasma alloying to even further reduce microbial growth and/or cross contamination in a clean room environment.

Thin Metal Coating of Molded Plastic Housings

Prior art housings for particle counters have been fabricated from plastic or metal depending on their intended market. While plastics offer light weight, low cost, widely variable shapes and sizes, bulk resistivity, and thermal insulation, metals, usually stainless steel, provide ruggedness and strength, conductivity both thermal and electrical, EMI shielding, static dissipation, resistance to a wide variety of chemicals especially organic solvents, and inhibition of microbial growth. Accordingly, in some embodiments, housings disclosed herein may be comprised of a combination of one or more polymers and one or more metal materials. In some embodiments, the housing may comprise one or more molded polymer parts, at least a portion of which are coated in a thin layer of metal.

Methods of applying the thin layer of metal include vacuum deposition processes, evaporation, PVD and sputtering. Thus, a coating of metal may be applied to surfaces of a plastic part endowing that part with the surface properties of the metal and the bulk properties of the plastic. The resulting enclosure may provide ESD protection, the appearance of metal (even brushed metal), and chemical resistance while being light weight and low cost. Therefore, in some embodiments, enclosures for particle counters may be made from plastic and coated with stainless steel, taking advantage of the best properties of both materials.

In one embodiment, a particle detection system comprises an inlet for receiving a particle-containing fluid; a sampling region for detecting particles, the sampling region in fluid communication with the inlet; an outlet for discharging the fluid, the outlet in fluid communication with the sampling region; and a housing at least partially enclosing the sampling region. The housing may comprise a molded polymer substrate; and a metal coating layer bonded to the molded polymer substrate such that at least some exterior surfaces of the housing are metal coated surfaces.

In one embodiment, the metal coating layer comprises stainless steel. In one embodiment, the metal coating layer comprises 316L stainless steel. In one embodiment, the metal coating layer comprises copper. In one embodiment, the metal coating layer comprises titanium. In one embodiment, the metal coating layer comprises silver. In one embodiment, the metal coating layer comprises at least one of: cobalt, nickel, zinc or zirconium.

In one embodiment, the metal coating layer has thickness of 0.01 mm to 1 mm. In one embodiment, the metal coating layer has thickness of 0.3 mm to 0.1 mm. In one embodiment, both the molded polymer substrate and the metal coating layer have a brushed texture. In one embodiment, both the molded polymer substrate and the metal coating layer have a nano-patterned or micro-patterned bacterial growth inhibitor texture.

In one embodiment, a method of reducing microbial contamination in a clean room comprises operating a particle detection system, the operating comprising: (a) introducing a particle-containing fluid to an inlet of the system; (b) sampling particles in the fluid in a sampling region of the system; (c) discharging the fluid via an outlet of the system; (d) introducing a first microbe onto a surface of a housing of the system, the housing at least partially enclosing the sampling region, wherein the housing comprises: a molded polymer substrate; and a metal coating layer bonded to the molded polymer substrate such that at least some exterior surfaces of the housing are metal coated surfaces; and (e) inhibiting growth of the first microbe or killing the first microbe via the metal coated surfaces.

In one embodiment, the system is an optical particle detector and the (b) sampling step comprises detecting particles via scattered light in the sampling region of the system. In one embodiment, the system is a microbial impactor, the particle-containing fluid contains biological particles, and the (b) sampling step comprises receiving at least a portion of the biological particles on an impact surface of the system; and growing at least some of the biological particles received by the impact surface.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and methods steps set forth in the present description. As will be obvious to one of skill in the art, methods and devices useful for the present methods can include a large number of optional composition and processing elements and steps.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every combination of components described or exemplified herein can be used to practice the invention, unless otherwise stated.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A particle detection system comprising:
   an inlet for receiving a particle-containing fluid;
   a sampling region for detecting particles, the sampling region in fluid communication with the inlet;
   an outlet for discharging the fluid, the outlet in fluid communication with the sampling region;
   a housing at least partially enclosing the sampling region, wherein the housing includes an exterior, the exterior comprising:
      a first antimicrobial surface wherein the first antimicrobial surface comprises an outer layer deposited on a stainless steel base layer, the outer layer comprising an antimicrobial component;
   herein the housing comprises a molded polymer substrate supporting the stainless steel base layer; and
   a touchscreen disposed in the housing, the touchscreen providing a user interface with the system, wherein the touchscreen comprises a second antimicrobial surface.

2. The system of claim 1, wherein the outer layer is an active screen plasma (ASP) deposited outer layer.

3. The system of claim 1 comprising a portable particle detection device.

4. The system of claim 1 comprising a particle sampler or a particle counter.

5. The system of claim 1 comprising a microbial impactor or an optical particle counter.

6. The system of claim 1, wherein the first antimicrobial surface comprises a different material as the second antimicrobial surface.

7. The system of claim 1, wherein the first antimicrobial surface, second antimicrobial surface or both are antibacterial surfaces.

8. The system of claim 1, wherein at least a portion of the first antimicrobial surface, second antimicrobial surface or both are provided as integral components of the system.

9. The system of claim 1, wherein at least a portion of the first antimicrobial surface, second antimicrobial surface or both are provided as one or more films or coatings.

10. The system of claim 1, wherein the second antimicrobial surface is a nano-patterned or micro-patterned bacterial growth inhibitor surface.

11. The system of claim 1, wherein the second antimicrobial surface comprises an antimicrobial polymer.

12. The system of claim 11, wherein the antimicrobial polymer comprises silver ions.

13. The system of claim 11, wherein the antimicrobial polymer comprises zinc.

14. The system of claim 1, wherein substantially all of the outer surfaces of the system are antimicrobial surfaces.

15. The system of claim 1, wherein substantially all of the outer surfaces of the touchscreen are antimicrobial surfaces.

16. The system of claim 1, wherein the housing comprises a handle, wherein substantially all of the outer surfaces of the handle are antimicrobial surfaces.

17. A method of reducing microbial contamination in a clean room, the method comprising:
operating a particle detection system, the operating comprising:
introducing a particle-containing fluid to an inlet of the system;
sampling particles in the fluid in a sampling region of the system;
discharging the fluid via an outlet of the system;
introducing a first microbe onto a first antimicrobial surface of a housing of the system, the housing at least partially enclosing the sampling region;
wherein the first antimicrobial surface comprises an outer layer deposited on a stainless steel base layer, the outer layer comprising an antimicrobial component;
wherein the housing comprises a molded polymer substrate supporting the stainless steel base layer; and
inhibiting growth of the first microbe or killing the first microbe via the first antimicrobial surface;
introducing a second microbe onto a second antimicrobial surface of a touchscreen of the system; and
inhibiting growth of the second microbe or killing the second microbe via the second antimicrobial surface of the touchscreen.

18. The method of claim 17, wherein the system is an optical particle detector, the sampling step comprising:
detecting particles via scattered light in the sampling region of the system.

19. The method of claim 17, wherein the system is a microbial impactor and wherein the particle-containing fluid contains biological particles, the sampling step comprising:
receiving at least a portion of the biological particles on an impact surface of the system; and
growing at least some of the biological particles received by the impact surface.

20. The method of claim 17, wherein the first microbe is a bacteria, a virus, a mold, or a fungus.

21. A particle detection system comprising:
an inlet for receiving a particle-containing fluid;
a sampling region for detecting particles, the sampling region in fluid communication with the inlet;
an outlet for discharging the fluid, the outlet in fluid communication with the sampling region; and
a housing at least partially enclosing the sampling region, wherein the housing includes:
an exterior, the exterior comprising:
a base layer comprising stainless steel;
an outer layer deposited on the base layer, the outer layer comprising a first antimicrobial surface, wherein the outer layer is an active screen plasma (ASP) deposited outer layer; and
a molded polymer substrate supporting the base layer and the outer layer, wherein the base layer is bonded to the molded polymer substrate; and
a touchscreen disposed in the housing, the touchscreen providing a user interface with the system, wherein the touchscreen comprises a second antimicrobial surface.

* * * * *